United States Patent
Dnyaneshwar

(10) Patent No.: US 7,329,421 B2
(45) Date of Patent: Feb. 12, 2008

(54) **PROCESS OF MANUFACTURING CLEAR JUICE FROM THE LEAVES OF THE *ALOE VERA* PLANT**

(76) Inventor: Agashe Mandar Dnyaneshwar, 242, Shaniwar Peth, Pune 411 030 (IN)

( * ) Notice: Subject to any disclaimer, the term of this patent is extended or adjusted under 35 U.S.C. 154(b) by 91 days.

(21) Appl. No.: 11/175,063

(22) Filed: Jul. 5, 2005

(65) Prior Publication Data

US 2006/0134238 A1    Jun. 22, 2006

(30) Foreign Application Priority Data

Dec. 16, 2004 (IN) .......................... 1349/MM/2004

(51) Int. Cl.
*A61K 36/886* (2006.01)
(52) U.S. Cl. ...................... 424/744; 424/725
(58) Field of Classification Search .................. None
See application file for complete search history.

(56) References Cited

U.S. PATENT DOCUMENTS 6,083,508 A * 7/2000 Avalos et al. ............... 424/744

2003/0064093 A1 * 4/2003 Jordan ........................ 424/449

* cited by examiner

*Primary Examiner*—Susan Coe Hoffman
(74) *Attorney, Agent, or Firm*—Charles A. Muserlian

(57) ABSTRACT

A process for manufacturing *aloe* gel from the leaves of the *Aloe vera* plant, comprising the following steps:
cleaning each leaf;
hand filleting each *aloe* leaf to separate the internal gel and leaving behind leaf residue;
collecting the internal gel in a stainless steel container;
Milling the gel in a multimill to obtain gel having particle size less than 1.5 mm;
adding charcoal in the range of 1% of the mass of the gel in particle size greater than 1.5 mm and mixing it well with the juice and pasteurizing the gel by heating the gel to about 70 to 75 degrees C. for about half an hour and;
prefiltering the juice to remove the charcoal;
adjusting the pH of the juice to lie on the range of 3.5 to 4 using lemon juice;
finally filtering of the pH adjusted juice using a filter bed and nutch filtration to remove even trace fibers from the juice;
filling the fiber free filtered juice in sterilized bottles and air tight sealing of the bottles;
autoclaving the sealed bottles in an autoclave at about 121° C. for about 30 minutes.

7 Claims, No Drawings

PROCESS OF MANUFACTURING CLEAR JUICE FROM THE LEAVES OF THE *ALOE VERA* PLANT

FIELD OF INVENTION

This invention relates to a process of manufacturing clear juice from the leaves of the *Aloe vera* plant.

This invention relates in particular to the manufacture of the juice with increased shelf life without the use of any artificial preservatives or additives.

BACKGROUND OF INVENTION

*Aloe*, a popular houseplant, has a long history as a multipurpose folk remedy. The healing properties of the *aloe* plant span back to ancient Egypt where herbal practitioners and healers recorded its use in promoting and restoring healthy skin.

There are over 240 different species of *Aloe*, growing mainly in the dry regions of Africa, Asia, Europe and America.

Some of the well known varieties are

1. *Aloe barbadensis* Mill.—(*A. vera* "L"; *A. vulgaris* Lamarck). This species, which is the source of Curacao *aloe*, has a very short, woody stem, lanceolate embracing leaves, of green color, with hard, pale spines. It has bright yellow flowers arranged in a spicate inflorescence. *barbadensis* is a native of southeastern Europe, northern Africa, and Madagascar. It is cultivated in Italy, Sicily, Malta, and especially in the West Indies.
2. *Aloe Perryi* Baker.—The true Socotrine *aloe* is a perennial herb, growing abundantly on the island of Socotra especially in the limestone tracts, from the sea level to an altitude of 3,000 feet and is also found in eastern Africa and in Arabia. It has a trunk one foot high which bears on its summit a dense rosette of pale green or reddish, succulent, lanceolate leaves with brown-tipped marginal spines.
3. *Aloe ferox* Miller.—One of the three South African, tree-like species yielding Cape *aloe*, is one of the tallest species of the genius. It has a forked stem 5 to 15 feet long, 4 to 6 inches in diameter; furnished at the top with a dense rosette containing 30 to 50 lanceolate leaves 1.5 to 2 feet long, with prickles.
4. *Aloe africana* Mill.—A South African species, has a simple tall trunk which bears on its summit a few triangular-oblong, glaucous, green leaves with large, horny marginal teeth. It is a native of the Cape Colony.
5. *Aloe spicata* Baker. (*A. Eru* var. *cornuta* Berger)—is a tall, branched aloe indigenous to tropical southern Africa. It possesses pale, glossy, fleshy leaves with white blotches and a panicle of campanulate yellow flowers."

*Aloe vera*, often called the "Natural healer", "Lily of the desert" or the "Plant of immortality", belongs to the *Aloe barbadensis* variety which has the best medicinal properties. It has been known and used for centuries because of its healing properties. The name *aloe* is derived from the Arabic word 'alloeh' meaning a shining bitter substance, which is found in *aloe* leaves.

The *Aloe vera* plant used in the present invention has the following botanical references:

Botanical name: *Aloe Barbadensis* Miller
Ayurvedic/Sanskrit name: Kumaari; Grihkanya; Ghritkumaarika; Kanya
Popular English name: *Aloe vera*
Habitat:
Cultivated throughout India, on the coasts of Maharashtra, Gujarat and South India. Native to eastern and southern Africa, *Aloe vera* grows wild in the tropics and is cultivated extensively worldwide.
Appearance: Although *Aloe vera* is a member of the Lily family, it is very cactus-like in appearance. It has lance shaped leaves with jagged edges and sharp points. A fully-grown plant stands around 60 to 90 cm high, and a mature leaf is 7 to 10 cm across at the base, weighing 1.5 to 2 kg. The *Aloe* leaf structure is made up of the following layers.
a) Rind—the outer protective layer;
b) Sap (Latex).
c) Mucilage (Gel).
Parts Used: Leaves.

The *Aloe* leaf contains over 75 nutrients and 200 active compounds, including 20 minerals, 18 amino acids, and 12 vitamins.

The uses of *Aloe vera* stem from these active ingredients. These substances harbor anti-inflammatory properties, which may explain why it has been reported to alleviate the pain and swelling associated with itches and burns. Some preliminary studies of *Aloe vera* suggest that it may be a powerful antiviral agent, and potent immune system enhancer. It is even being tested as a possible treatment for certain types of cancer and conditions as serious as diabetes.

Uses of *Aloe vera*:

External Uses: The *aloe* plant's healing powers are most widely known for use in the following areas:
a) Treating skin conditions: These conditions include psoriasis, shingles, and others associated with itching.
b) Beauty treatment:
*Aloe vera* has a long history in use for beauty therapies. Cleopatra is said to have attributed her beauty to it. Even today *aloe* is used in several preparations like moisturizing creams, lotions, hair care preparations like shampoo's etc.
c) First aid: *Aloe vera* is an excellent first aid remedy to keep in the home for wounds, abrasions, burns, scrapes, scalds, and sunburn. Leaf on breaking releases soothing gel, which may be applied topically to the affected part.
d) Skin conditions: *Aloe vera* is useful for almost any skin condition that needs soothing and astringing, and will help varicose veins to some degree. *Aloe* gel has been used for topical treatment of skin irritations.
e) Embalming: The juice of *aloes* was formerly used in Eastern countries in embalming and to preserve dead bodies from putrefaction.
Internal Uses:
a) Laxative: At low doses, the bitter properties of the herb stimulate digestion. At higher doses they are laxative and purgative.
b) Dentistry: It is extremely useful in the treatment of gum disease; it reduces the bleeding of the gums; it is powerfully antiseptic in gum pockets and its antifungal properties help greatly in the problem of denture stomatitis.
c) In homeopathy: *Aloe* has been used in homeopathic medicine from early times both as a purgative and tonic. It is used to treat congestion, especially in the pelvic organs, abdomen, and head; for example minor prolapse of the uterus, prostrate problems, constipation and headaches. It is also useful for diarrhea with painful urination brought on by food intolerance. This is a common remedy for people who have a very sedentary lifestyle, especially the elderly and those who suffer from fatigue.
d) Other uses: It is useful for a number of skin conditions, especially psoriasis, where the process of internal detoxification is deemed by naturopaths to be important. *Aloe* products for internal use have also been promoted for abscess, acne, balantis, coughs, diabetes, cancer, Herpes, headaches, arthritis, ulcers, irritable bowel syndrome, immune-system deficiencies and many other conditions.

When taken internally, *Aloe vera* has a 'cleansing' effect on the body, by virtue of its action on the digestive tract.

*Aloe vera* appears to be a considerably safe herb, with no known toxicity when used in moderation. However there are some reports of side effects at higher doses which can include abdominal pain, diarrhea, and electrolyte imbalances.

*Aloe* is the source of two products that are completely different in their chemical composition and their therapeutic properties but which have very similar names namely the *Aloe vera* gel and the *Aloe vera* latex.

The products from the *Aloe vera* plant are can essentially be divided into those, which predominantly contain either the latex or the gel.

The *Aloe vera* Latex: The Leaves exude a bitter liquid, which is dried and known as "bitter *aloes*, which forms the latex. These are contained in the pericyclic tubules. These specialized cells known as pericyclic tubules are specialized cells that occur just beneath the epidermis or rind of these same leaves. The yellow latex is bitter and is dried to produce a pharmaceutical product, which is an active cathartic. This bitter fluid helps protect the plant from animals.

The latex contains anthraquinone and anthrones, which are strongly laxative. (They probably act by increasing colonic peristalsis and increasing the intestinal water content by opening chloride channels of the colonic membrane to cause a net reduction of liquid absorption by the colon). For pharmaceutical use as a laxative, the latex is often dried to produce "*aloe*" granules that are dark brown from exposure to air.

*Aloe vera* gel is the leaf pulp or mucilage. It is a thin clear jelly-like substance obtained from the parenchymal tissue that makes up the inner portion of the leaves.

It is prepared from the leaf by various procedures, all of which involve its separation not only from the inner cellular debris but, also from the other active component which forms the yellow latex.

This gel consists of 95% water and the other ingredients form the remaining 5%.

a) The gel contains the 8 essential Amino acids that the human body needs but cannot manufacture. (There are 20 "critical" Amino Acids in human metabolism, but the body can only make 12, the other 8 have to be obtained from food).

These are: Isoleucine, Leucine, Lysine, Methionine, Phenylalanine, Threonine, Valine, and Tryptophan. All these are contained in *Aloe vera*;

b) Enzymes—Amylase, Bradykinase, Catalase, Cellulase, Lipase, Oxidase, Alkaline Phosphatase, Proteolytiase, Creatine Phosphokinase, Carboxypeptidase. Most of these are beneficial for human metabolism;

c) Lignin—Gives *Aloe vera* its penetrating powers, but is not considered to have any other benefit.

d) Minerals—Calcium, Chromium, Copper, Iron, Magnesium, Manganese, Potassium, Phosphorous, Sodium, and Zinc. During the present times due to intensive farming on mineral depleted soils our diet is mostly mineral deficient. Many bodily functions depend on minerals to work properly, and some minerals are critical to the metabolism of vitamins.

e) Mono- and Poly-Saccharides—The mono-saccharides are the familiar glucose, and fructose that are known as sugars. The more complex long-chain sugars are the poly-saccharides which are thought to give *Aloe vera* its unique healing and immuno-stimulating properties;

f) Salicylic Acid—A substance similar to aspirin that can help reduce fever and inflammation.

g) Saponins—Natural, soapy substances that have both cleansing and antiseptic properties;

h) Sterols—Naturally occurring plant steroids with analgesic, anti-inflammatory, and antiseptic properties.

i) Vitamins—These include A (beta-carotene and retinol), B1 (thiamine), B2 (riboflavin), B3 (niacin), B6 (pyridoxine), B12 (cyanocobalamin), C (ascorbic acid), E (tocopherol) and Folic Acid.

The inner part of the leaf is filleted out to get pure *Aloe vera* gel. *Aloe* gel is sometimes contaminated with *aloe* latex, if the separation is not done properly, thus inducing an unwanted laxative effect following consumption of the gel.

The *Aloe* gel (mucilage) is used both externally and internally.

External Use:

a) Fresh gel: The leaf is split and the gel is applied directly to burns, wounds, dry skin, fungal infections, and insect bites.

Extensive research since the 1930s in the US and Russia has shown that the clear gel has a dramatic ability to heal wounds, ulcers, and burns, putting a protective coat on the affected area and speeding up the rate of healing. This action is in part due to the presence of aloectin B, which stimulates the immune system.

b) Ointment—Split several leaves to collect a large quantity of gel, and boil it down to a thick paste. Can be stored in clean jars in a cool place and used like the fresh leaves.

Internal Use:

a) Inhalation: The gel is used in steam inhalants for bronchial congestion. Lozenges:

b) Tonic wine: Fermented aloe gel with honey and spices is known as 'kumaryasava' in India and is used as a tonic for anemia, poor digestive function, and liver disorders.

c) Raw leaves: Raw leaves can be eaten either fresh or preserved

Up to 2 tsp of the *Aloe* gel in a glass of water or fruit juice, three times a day, can be taken as a health tonic.

d) *Aloe* drink: These days *Aloe* has become very popular as a beverage because of the enormous health benefits it offers.

A high quality *Aloe* Drink, which uses only the nutritious inner gel—not the outer rind of the leaf, is one of the most nutritious drinks available.

Unlike the inner gel, the rind of the leaf has essentially no nutritional value. This means that the presence of the rind in products such as drinks is little more than 'filler' and if contaminated with the latexit can induce an unwanted laxative effect. Therefore the promotion of "whole leaf," or products with the rind included, as being more beneficial in some way—is simply incorrect and misleading.

While there are good *aloe*-based drinks with the rind included, *Aloe* Drinks without the essentially useless rind are free from this needless filler and are more beneficial.

Some benefits of *Aloe vera* juice when taken internally:

Helps heartburn, stomach ulcer, colitis, Crohn's disease, diverticulitis; indigestion and other intestinal problems;

Fights colds, flu, and other viral infections;

Reduces tumors, malignant and benign;

Reduces allergies;

Helps arthritis, lupus, bursitis, etc;

Helps chronic fatigue conditions;

Aids in detoxification.

Prior Art

The mechanical separation process of separating the gel and latex is not always complete, so *aloe* latex can be found in some *aloe* gels. It is desirable to make the gel as pure as possible, because *aloe* latex contains the anthraquinone glycosides 'aloin' A and B, which are potent laxatives. The processed products are also difficult to keep stable, a problem that can cause differences in product potency. Many products advertise special stabilizing procedures, but the best source of the *aloe* gel would be direct from a broken leaf of the plant.

Within each leaf is a clear, semi-liquid pulp, which botanists call parenchyma (tissue composed of soft, thin-walled cells). The removal of the outer leaf to retain only the clear gel is called filleting.

The pulp, which contains the gel, is removed in a 'filleting' process. It is extracted with care to avoid contaminating it with bitter sap.

Methods of Separating the Juice/Gel From the Leaf:

1) Some methods of preparing *Aloe vera* products involve solvent extraction, often with harsh physical and chemical treatments, resulting in a gel that is hardly representative of the fresh *aloe*, and may be as little as 15% *Aloe vera*.
2) One of the most common methods of preparing *Aloe vera* juice involves filleting the leaf by removing the green outer portion, which contains the 'aloin', and leaving just the gel that exists in the leaf. The gel hangs together by itself when the leaf is first filleted. Within a few minutes, the enzymes in the gel break the structure down so that it becomes a running fluid instead of a standing gel. The juice at this point of time has a typical, strong *aloe* flavor. The *aloe* leaves are filleted just outside the fields soon after they're collected.
Then the juice is stabilized using different methods
3) When the plant is filleted, the very bitter-tasting 'aloin' that is in the outer epidermis of the leaf and the inner lining of the gel is removed, representing between five and ten percent of the gel. To avoid this loss, sometimes the whole *aloe* leaf is crushed. It is much cheaper to crush the leaves than to fillet each leaf separately. When that is done, the 'aloin' is retained, which makes the juice extremely bitter.
4) Another method starts with the pulverized whole leaf. Processes known to those skilled in the art are used to dissolve the cellulose, eliminate contaminants, and remove 'Aloin' and '*Aloe* Emodin' (which cause diarrhea). The resulting gel, which is 99.52% water, is concentrated by using cool, heat-free evaporative techniques to remove excess water.

Methods of Preserving the Gel or Juice Obtained From the Leaf:

The *aloe* juice is a good nutrient. For the same reason bacteria and other micro-organisms also thrive upon it if due care is not taken. Therefore it is very important to stabilize the juice. This is done in the prior art by the use of preservatives (Chemical means) or by heating in different ways (physical means) to kill the micro-organisms and thereby increase the shelf life of the juice.

*Aloe vera* clear juice processing is commonly strabilized in the prior art as follows 1] WASHING OF *ALOE* LEAVES: Done using hot water to remove dust, soil and other foreign matter.
2] FILLETING OF LEAVES: is done mechanically
3] SIZING OF THE PULP: The inner gel is sized using multimill to get fibrous juice.
4] pH ADJUSTMENT: pH of juice which is initially 4.5 to 5.0 is adjusted to 3.5-4.0 using citric acid.
5] PASTEURISATION: Pasteurisation by heating juice at 70 deg centigrade for 30 mins.
6] PREFILTRATION: Fibrous juice is filtered using centrifuge to get the raw *Aloe* juice.
7] PRESERVATION & FINAL FILTRATION Preservatives are added as follows, Sodium benzoate . . . 0.2% Potassium sorbate . . . 0.2% Final filteration through nutch filter done to get clear, white *Aloe* juice.
8] FILLING: Final *Aloe* juice filled in bulk containers.
9] TESTING AND FINAL PACKING: Testing done as per Quality Control specs. Final packing done after the release.

Observations on the Final Art Process Steps

Preservation by Chemical Means a) Ascorbic acid found in vitamin C:
Toxicity does not normally occur, as vitamin C is water-soluble and is regularly excreted by the body. Recent studies have shown, however, that excessive doses of vitamin C (many times more than the recommended amount) can lead to toxicity).

The most common manifestations of vitamin C toxicity are kidney stones, and in very rare circumstances, anemia (caused by interference with vitamin B12 absorption).

High levels of Vitamin C also may cause Diarrhea, abdominal cramps, high stomach acid, increased urination, insomnia, irritability, joint pains, osteoporosis, headaches, hypoglycemia, weakness, anemia, PMS, may increase infections by causing copper deficiency, reduced estrogen, reduced progesterone and reduced prolactin.

b) Citric acid: It is a common preservative but in higher doses it is suspected to cause diarrhea, nausea, vomiting, stomach pain, fluid retention, convulsions, unusual weakness, mental confusion, tingling or numbness of the hands or feet.

c) Sodium benzoate.
Although it is not known to be toxic, limits of sodium benzoate in food have to be considered as it tends to impart a taste that will make some foods unacceptable.

d) Potassium Sorbate: It is widely used in the food industry and is the potassium salt of sorbic acid, a naturally occurring organic acid. It has been used extensively as a fungi static agent for foods such as baked goods, glazed cherries, chocolate products, carbonated drinks and pie fillings.

Adverse reactions include irritation of the eyes, nose, throat and skin. It may result in dermatitis, wheals, erythema and urticaria and may cause a mild skin irritation among sensitive individuals e) U.S. Pat. No. 3,892,853 discloses a method to stabilize gel by adding catalytic portions of a nontoxic oxidant and heating the gel from 35° C. to about 80.° C., the processed gel is then buffered to maintain a pH in the range of 4 to 8. Other ingredients may also be added to achieve desired or cosmetic purposes.

f) U.S. Pat. No. 4,178,372 discloses a process for stabilizing *Aloe vera* gel utilizing a non-toxic oxidant, heating the gel from about 35.° C. to about 80.° C., after which ascorbic acid and a buffer is added to produce a hypoallergenic stabilized *Aloe vera* gel.

Ascorbic acid as mentioned earlier has its set of adverse effect when used in excess.

Thus although diff types of stabilizers/preservatives can be used they have their limitations if the health drink is to be consumed on a regular basis. In such case the preservative or stabilizers may also be inadvertently consumed in excess to the safe quantities.

Preservation by Physical Means

Another Set of Methods of Stabilizing Include a) Flash Cooling: As a crucial step to preserve biological activity, the gel is cooled to below 5° C. in ten to fifteen seconds following the gel extraction. Rapid cooling not only slows enzymatic and microbial deterioration of the gel, but also aids in reducing the microbial counts in the product. This is followed by Pasteurization by which the biological activity remains essentially intact when the gel is heated at 65° C. for periods of less than fifteen minutes.

However extended periods or higher temperatures result in greatly reduced activity levels. Higher vacuums and temperatures will also cause activity loss as will extended concentration times.

b) Several processes have been provided to prolong the effective life of the *Aloe vera* extract. These attempts include U.S. Pat. No. 3,878,179 which discloses a process for the extraction and stabilization of the *Aloe vera* gel by treating it under ultra violet radiation at ambient temperature to produce a biologically sterile and chemically stable extract. However on the flip side short-wave UV light is hazardous to workers. Also Very short wavelengths of UV light are weakly ionizing and can cause the formation of ozone, a strong oxidizing agent, which is not only toxic to humans but is capable of damaging equipment over long periods of exposure. UV light also presents skin and eye burn hazard, and factors such as lamp age and poor maintenance can reduce performance c) Dry and Moist heat: To sterilize by dry heating, an object must be heated at 160 degrees C. for 60 minutes. In case of moist heat Micro-organisms heated in the presence of water or steam. Here micro-organisms are killed at temperatures much lower than that used for dry heat sterilization. There are two problems with this method: first, heating water to temperatures higher than 100° C. causes it to boil and evaporate, second, many bacteria form spores that are not killed by exposure to temperatures of 100° C., even in the presence of water. Such spores can only be killed by dry heat at 160 degrees C. for 60 minutes, or by exposure to moist heat at 121 degrees C. for 15 minutes.

Such high temperatures in an exposed state where a portion of the water content of the gel evaporates and the heated gel is contacted with ambient conditions alters the effectiveness of the active ingredients.

Disadvantages also include the much longer processing time, the possibility of damage to some ingredients, and the higher temperatures that pose an added hazard to operators. Additional problems exist because of operator error, including failure to process for the required time, improper loading of items, failure to preheat the chamber, and opening the oven during operation, which interrupts the cycle, requiring that the process be restarted from the beginning.

SUMMARY OF THE INVENTION

The object of this invention is to provide a novel method for processing *Aloe vera* gel to obtain *Aloe vera* juice.

It is also the object of this invention is to manufacture *Aloe vera* clear juice by a process where the internal fillet (gel) is separated from the leaf residue by hand filleting thereby ensuring that the gel is in no way contaminated with the unwanted latex It is another object of the present invention to increase the shelf life of the *Aloe vera* juice without the use of preservatives.

It is yet another object of the present invention to increase the shelf life of the *Aloe vera* juice obtained by subjecting it to controlled temperature and pressure conditions thereby significantly improving the shelf life of the product.

It is envisaged in accordance with this invention that *Aloe vera* juice is autoclaved inder carefully controlled conditions.

Auto claving: Industrial autoclaves are called retorts.

In autoclaves, steam can be trapped and heated to high temperatures. As heat is applied to steam the pressure builds up inside the autoclave and the temperature increases. At zero pounds of steam per square inch above standard atmospheric pressure the temperature of steam in the autoclave is 100° C., but by the time the pressure has reached 15 psi the temperature of the steam in the autoclave is at 121° C.

This is enough to kill nearly all bacterial spores.

Autoclaving advantage:

The process makes use of passive steam that does not create damaging differential pressure during the process.

Penetration of sterile glassware, media and instruments is achieved.

Decontamination of reusable supplies and equipment.

Decontamination of infectious waste.

The advantages of autoclaving are that it is relatively fast, can be used with packaging, processes a wide range of materials without destruction, and is reliable.

Due to all the above reasons it has been discovered by the inventor that autoclaving seems to be the method of choice for preservation to increase the shelf life of the products.

STATEMENT OF THE INVENTION

According to this invention there is provided a process for manufacturing aloe gel from the leaves of the *Aloe vera* plant, comprising the following steps:

cleaning each leaf;

hand filleting each aloe leaf to separate the internal gel and leaving behind leaf residue;

Collecting the internal gel in a stainless steel container;

Milling the gel in a multimill to obtain gel having particle size less than 1.5 mm;

adding charcoal in the range of 1% of the mass of the gel in particle size greater than 1.5 mm and mixing it well with the juice and pasteurizing the gel by heating the gel to about 70 to 75 degrees C. for about half an hour and;

Prefiltering the juice to remove the charcoal;

Adjusting the pH of the juice to lie on the range of 3.5 to 4 using lemon juice;

finally filtering of the pH adjusted juice using a filter bed and nutch filtration to remove even trace fibres from the juice;

filling the fibre free filtered juice in sterilized bottles and air tight sealing of the bottles;

autoclaving the sealed bottles in an autoclave at about 121° C. for about 30 minutes.

Typically, the step of cleaning each leaf includes the step of sorting and washing the *aloe* leaves using hot water having a temperature range of 70-80° C. for a period of one hour.

Typically, the step of filleting includes Cutting open the *aloe* leaves from the sides and then in the middle transversely using a knife; and separating the gel from the green leafy portion.

Typically, the milling operation is performed in a multi-mill for about 15 minutes having a screen of mesh size 1.5 mm.

Typically, the step of prefiltering is done in a centrifuge machine.

Typically, the step of autoclaving is done under pressure of about 10 to 15 psi.

Preferably, the step of autoclaving includes filling the juice in 100 ml bottles.

DETAILED DESCRIPTION OF THE INVENTION

Description of the equipment used in the manufacturing process.
a) Autoclaves: Autoclaves offer fast, safe, dependable, and convenient steam sterilization. Steam sterilization is the most advisable method of sterilization when dealing with non-thermo labile products, i.e. those that resist the conditions of temperature and humidity of this method. It is mainly used in the pharmaceutical industry and in biotechnology for sterilizing.
Application: Sterilization of liquids, media, instruments, glassware, clothing, and waste
b) Hiflow bed: It is a brand name for filter aids. One of the most widely used and robust means of micro-particulate separation in liquid systems today is highly porous powdered media, often called filter aids.

It frequently offers the lowest cost option in any filtration process. Filter aids are used in conjunction with a variety of filtration equipment to enhance or enable to solid-liquid separations.

PREFERRED EMBODIMENTS OF THIS INVENTION

1] WASHING OF *ALOE* LEAVES: typically a batch of About 30 Kgs of *Aloe vera* leaves are taken, preferably fresh. The leaves are prepared for filleting by cleaning the *aloe* leaf with hot water (70° C. to 80° C.) This is done for about 1 hour.
2] FILLETING OF LEAVES:
Comprises the following steps:
By cutting open the leaves from the sides and then in the middle transversely;
Separating the gel from the green leaf portion, and collecting the gel in SS containers.
The gel so collected is sent for milling operation
The above processes are completed in about 1 hour.
The quantity of pulp obtained is about 16 Kgs.
3] SIZING OF THE PULP (INNER GEL): Multi mill of mesh size of about 1.5 mm is used for sizing the gel. This process is done for 15 minutes The quantity of pulp obtained is about 15 Kgs.
4] PASTEURISATION & CHARCOAL TREATMENT OF JUICE: The sized fibrous juice is collected in a SS jacketed vessel where the juice is heated to about 70° C. for half an hour. Simultaneously 1% charcoal is added and mixed well. This process is done for 35 minutes This is done at a temperature of 70-75° C.
5] PREFILTRATION: The fibrous juice is filtered using a centrifuge. This process takes about 10 minutes
6] pH ADJUSTMENT: 0.020 kgs. of Lemon juice is added and the final pH of the resultant juice is checked to be in the range of 3.5 to 4.0. This takes about 20 minutes.
7] FINAL FILTRATION: The resultant juice is filtered using hiflow bed first and then through Nutch filters to get the clear white *aloe* juice. This takes about 45 minutes. The quantity of pulp obtained is about 11 Kgs.
8] BOTTLE WASHING, FILLING & SEALING:
In one batch about 100 Glass bottles are washed using potable water and rinsed with distilled water.
The filling machines and the manufacturing areas are cleaned before filling the bottles. 100 ml to 103 ml of clear *Aloe* juice is filled into the cleaned bottles using filling machine. Sealing is done with washed and sterilized rubber bungs and tear-off aluminium seals.
9] AUTOCLAVING: The filled and sealed *Aloe vera* juice are loaded Done at 121° C., under 10-15 psi pressure for 30 minutes.
The juice is filled in bottles (100 ml each) and closed with rubber bung and tear off aluminium seals and loaded into the autoclave, where they are subjected to a temperature of 121° C. and pressure of 10 psi for a period of half an hour. Then the autoclave is switched off and allowed to cool to room temperature.
10] TESTING AND FINAL PACKING
The final products is tested by a visual test for purity microbial content and pH. The autoclaved bottles are then transferred to the final package area where they are labeled, shrunk wrapped and packaged in corrugated boxes.

Precautions to be Taken During the Manufacturing Process.
1) Quality and quantity of purified water is checked before use in each batch. It should be free from any impurities.
2) The materials are neither touched nor handled with bare hands. Face masks and rubber gloves are always used while handling the materials.
3) Before starting every batch, it is checked that no materials of the previous batch are present in the manufacturing area.
4) It is ensured that the temperature does not exceed above 85° C. for water and oil phase.

EXAMPLE-1

1] WASHING OF *ALOE* LEAVES: 30 Kgs of *Aloe vera* leaves were taken. The leaves were prepared for filleting by cleaning the *aloe* leaf with hot water (75° C.). This was done in 1 hour and 10 minutes.
2] FILLETING OF LEAVES: Comprised of the following steps:
The leaves were cut open from the sides and then in the middle transversely;
The gel was separated from the green leafy portion, and the gel was collected in SS containers.
The gel so collected was sent for milling operation The above processes were completed in 1 hour and 5 minutes.
The quantity of pulp obtained was 16.3 Kgs.
3] SIZING OF THE PULP (INNER GEL): Multi mill of mesh size of 1.5 mm was used for sizing the gel. This process is done for 15 minutes The quantity of pulp obtained was 15.2 Kgs.
4] PASTEURISATION & CHARCOAL TREATMENT OF JUICE: The sized fibrous juice was collected in a SS jacketed vessel where the juice was heated to 71° C. for half an hour. Simultaneously 1% (0.15 Kgs) charcoal was added and mixed well. This process is done for 35 minutes This is done at a temperature of 71° C.
5] PREFILTRATION: The fibrous juice was filtered using a centrifuge. This process took 11 minutes 6] pH ADJUSTMENT: 0.020 kgs of Lemon juice was added and the final pH of the resultant juice was adjusted and checked to be 3.7. (It has to be within the range of 3.5 to 4.0). This took 20 minutes.

7] FINAL FILTRATION: The resultant juice was filtered using hiflow bed first and then through Nutch filters to get the clear white aloe juice. This takes 43 minutes. The quantity of pulp obtained is about 11.2 Kgs.

8] BOTTLE WASHING, FILLING & SEALING: 100 Glass bottles were washed using potable water and rinsed with distilled water. The filling machines and the manufacturing areas were cleaned before filling the bottles. 100 ml to 103 ml of clear *Aloe* juice was filled into the various cleaned bottles using filling machine. Sealing was done with washed and sterilized rubber bungs and tear off aluminium seals.

9] AUTOCLAVING:
The juice filled in bottles above were loaded into the autoclave, where they were subjected to a temperature of 121° C. and pressure of 10 psi for a period of half an hour. Then the autoclave was switched off and allowed to cool to room temperature.

10] TESTING AND FINAL PACKING: Testing was done as per Q.C specifications. The autoclaved bottles were then transferred to the final package area where they were labeled, shrunk wrapped and packaged in corrugated boxes

EXAMPLE-2

1] WASHING OF *ALOE* LEAVES: 40 Kgs of *Aloe vera* leaves were taken. The leaves were prepared for filleting by cleaning the *aloe* leaf with hot water (75° C.). This was done in 1 hour and 5 minutes.

2] FILLETING OF LEAVES: Comprised of the following steps:
The leaves were cut open from the sides and then in the middle transversely;
The gel was separated from the green leafy portion, and the gel was collected in SS containers.
The gel so collected was sent for milling operation
The above processes were completed in 1 hour.
The quantity of pulp obtained was 19. Kgs.

3] SIZING OF THE PULP (INNER GEL): Multi mill of mesh size of 1.5 mm was used for sizing the gel. This process is done for 15 minutes The quantity of pulp obtained was 17.8 Kgs.

4] PASTEURISATION & CHARCOAL TREATMENT OF JUICE: The sized fibrous juice was collected in a SS jacketed vessel where the juice was heated to 73° C. for half an hour. Simultaneously 1% (0.178 Kgs) charcoal was added and mixed well. This process is done for 35 minutes This is done at a temperature of 73° C.

5] PREFILTRATION: The fibrous juice was filtered using a centrifuge. This process took 10 minutes 6] pH ADJUSTMENT: 0.022 kgs of Lemon juice was added and the final pH of the resultant juice was adjusted and checked to be 3.8. (It has to be within the range of 3.5 to 4.0). This took 22 minutes.

7] FINAL FILTRATION: The resultant juice was filtered using hiflow bed first and then through Nutch filters to get the clear white *aloe* juice. This takes 44 minutes. The quantity of pulp obtained is about 13.5 Kgs.

8] BOTTLE WASHING, FILLING & SEALING: 100 Glass bottles were washed using potable water and rinsed with distilled water. The filling machines and the manufacturing areas were cleaned before filling the bottles. 100 ml to 103 ml of clear *Aloe* juice was filled into the various cleaned bottles using filling machine. Sealing was done with washed and sterilized rubber bungs and tear off aluminium seals.

9] AUTOCLAVING: The juice filled in bottles above were loaded into the autoclave, where they were subjected to a temperature of 121° C. and pressure of 10 psi for a period of half an hour. Then the autoclave was switched off and allowed to cool to room temperature.

10] TESTING AND FINAL PACKING: Testing was done as per Q.C specifications. The autoclaved bottles were then transferred to the final package area where they were labeled, shrunk wrapped and packaged in corrugated boxes.

The invention claimed is:

1. A process for manufacturing *aloe vera* juice from the leaves of the *Aloe vera* plant, comprising the following steps:
   a) cleaning each *Aloe vera* leaf;
   b) hand filleting each aloe leaf to separate the internal gel and leaving behind leaf residue;
   c) collecting the internal gel in a stainless steel container;
   d) milling the internal gel in a multimill to obtain a gel having particle size less than 1.5 mm;
   e) adding charcoal in the range of 1% of the mass of the gel in step d), wherein the charcoal has a particle size of greater than 1.5 mm and mixing the contents well;
   f) heating the mixture obtained in step e) to about 70 to 75° C. for about half an hour to convert the gel into a juice;
   g) filtering the mixture obtained in step f) to separate the juice and the charcoal;
   h) adjusting the pH of the juice obtained in step g) to about 3.5 to 4 using lemon juice;
   i) filtering the pH adjusted juice obtained in step h) using a filter bed to remove trace fibers and obtain a fiber-free juice;
   j) filling the fiber-free juice obtained in step i) in sterilized bottles and air tight sealing of the bottles;
   k) autoclaving the sealed bottles in an autoclave at about 121° C. for about 30 minutes.

2. The process for manufacturing *aloe vera* juice from the leaves of the *Aloe vera* plant, as claimed in claim 1, in which the step of cleaning each leaf includes the step of sorting and washing the *aloe* leaves using hot water having a temperature range of 70-80° C. for a period of one hour.

3. The process for manufacturing *aloe vera* juice from the leaves of the *Aloe vera* plant, as claimed in claim 1, in which the step of filleting in step b) includes cutting open the aloe leaves from the sides and then in the middle transversely using a knife; and separating the gel from the green leafy portion.

4. The process for manufacturing *aloe vera* juice from the leaves of the *Aloe vera* plant, as claimed in claim 1, in which the milling operation of step d) is performed in a multimill for about 15 minutes having a screen of mesh size 1.5 mm.

5. The process for manufacturing *aloe vera* juice from the leaves of the *Aloe vera* plant, as claimed in claim 1, in which the step of filtering in step g) is done in a centrifuge machine.

6. The process for manufacturing *aloe vera* juice from the leaves of the *Aloe vera* plant, as claimed in claim 1, in which the step of autoclaving in step k) is done under pressure of about 10 to 15 psi.

7. The process for manufacturing *aloe vera* juice from the leaves of the *Aloe vera* plant, as claimed in claim 1, wherein the *aloe vera* juice is filled in 100 ml bottles and then autoclaved.

* * * * *